(12) United States Patent
Matsukawa et al.

(10) Patent No.: US 8,696,580 B2
(45) Date of Patent: Apr. 15, 2014

(54) ARTERIOSCLEROSIS EVALUATING APPARATUS

(75) Inventors: Mami Matsukawa, Kyoto-fu (JP);
Yoshiaki Watanabe, Kyoto-fu (JP);
Masashi Saito, Kyoto-fu (JP); Takaaki Asada, Shiga-ken (JP); Mio Furuya, Kyoto-fu (JP)

(73) Assignees: The Doshisha, Kyoto (JP); Murata Manufacturing Co., Ltd., Kyoto (JP)

( * ) Notice: Subject to any disclaimer, the term of this patent is extended or adjusted under 35 U.S.C. 154(b) by 128 days.

(21) Appl. No.: 13/037,028

(22) Filed: Feb. 28, 2011

(65) Prior Publication Data
US 2011/0208073 A1   Aug. 25, 2011

Related U.S. Application Data

(63) Continuation of application No. PCT/JP2009/065125, filed on Aug. 29, 2009.

(30) Foreign Application Priority Data

Sep. 1, 2008 (JP) ................................ 2008-223847

(51) Int. Cl.
*A61B 5/02* (2006.01)
(52) U.S. Cl.
USPC ........... 600/455; 600/485; 600/490; 600/494; 600/500; 600/502
(58) Field of Classification Search
USPC .................. 600/455, 485, 490, 494, 500, 502
See application file for complete search history.

(56) References Cited

U.S. PATENT DOCUMENTS

| 5,961,467 A * | 10/1999 | Shimazu et al. | 600/485 |
| 6,612,993 B2 * | 9/2003 | Narimatsu | 600/500 |
| 6,712,768 B2 * | 3/2004 | Ogura et al. | 600/494 |
| 2004/0064055 A1 * | 4/2004 | Kawaguchi | 600/490 |
| 2005/0283086 A1 * | 12/2005 | Satoh et al. | 600/500 |

FOREIGN PATENT DOCUMENTS

| JP | 2003-079586 A | 3/2003 |
| JP | 2004-113593 A | 4/2004 |
| JP | 2006-158426 A | 6/2006 |
| JP | 2008-228934 A | 10/2008 |

OTHER PUBLICATIONS

International Search Report; PCT/JP2009/065125; Sep. 29, 2009.

* cited by examiner

*Primary Examiner* — Christopher D Koharski
*Assistant Examiner* — Natasha Patel
(74) *Attorney, Agent, or Firm* — Studebaker & Brackett PC

(57) ABSTRACT

The disclosed is an arteriosclerosis evaluating apparatus capable of easily separating pulse wave data detected at one measurement site into an incident wave and a reflected wave and capable of easily determining and evaluating the degree of arteriosclerosis. The pulse wave transmitted through an artery is detected at one site of a living body by a pulse wave detection device, and the detected pulse wave is fitted with a fitting function by a breakdown device so that the detected pulse wave can be broken down into an incident wave and a reflected wave. The degree of arteriosclerosis is evaluated from the amplitude intensities (i.e., peak intensities) of the incident wave and the reflected wave broken down from the pulse wave.

20 Claims, 10 Drawing Sheets

F I G. 1
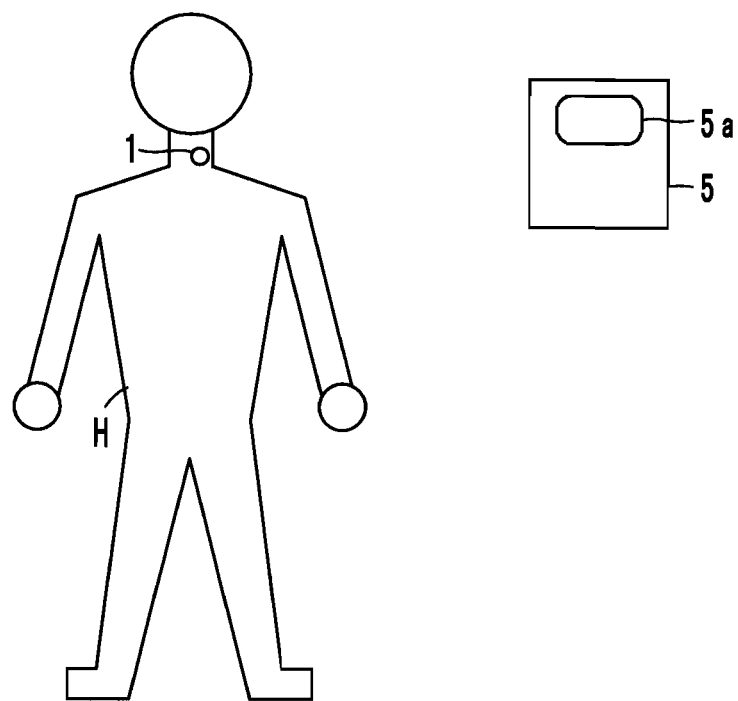
F I G. 2
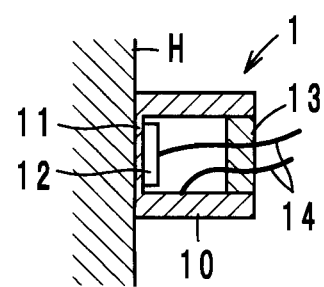

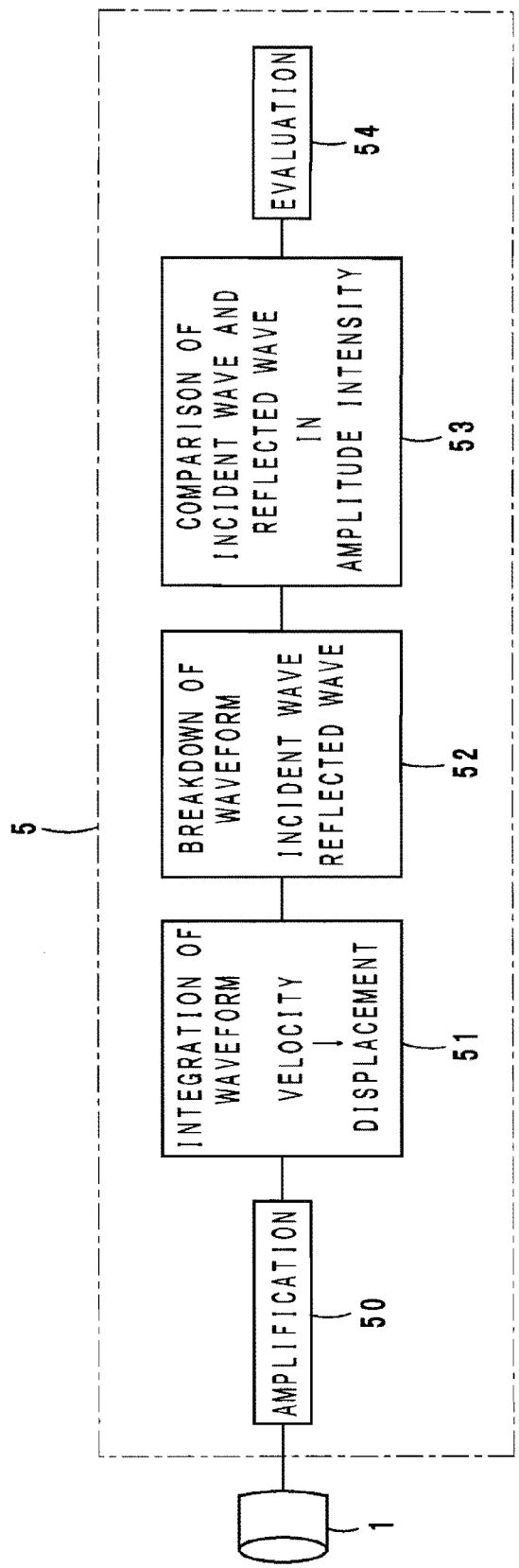

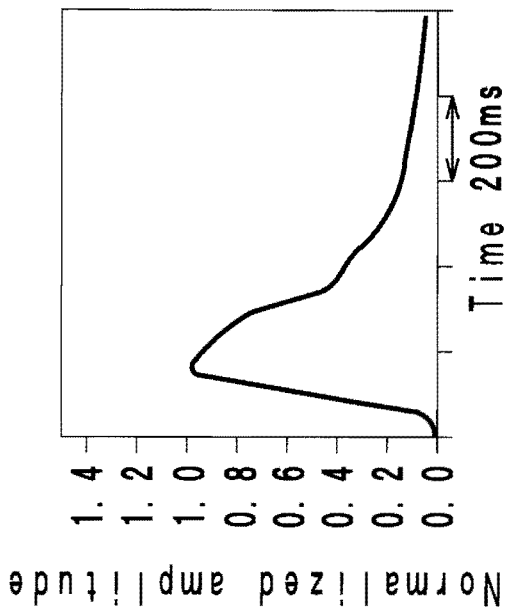
FIG. 6(a) MODEL FUNCTION FOR YOUNG PEOPLE
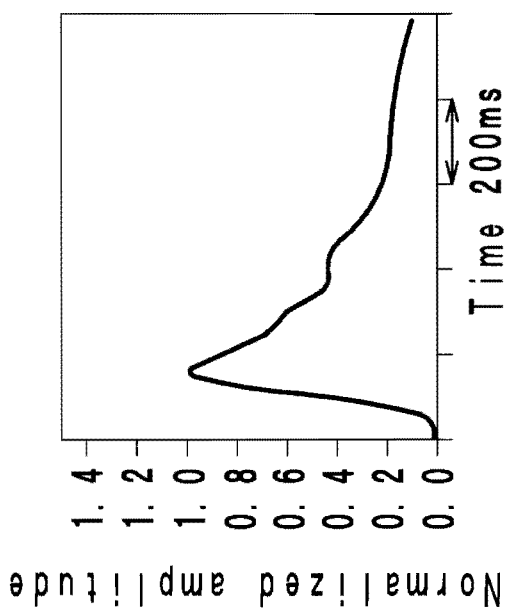
FIG. 6(b) MODEL FUNCTION FOR OLD PEOPLE F I G. 9
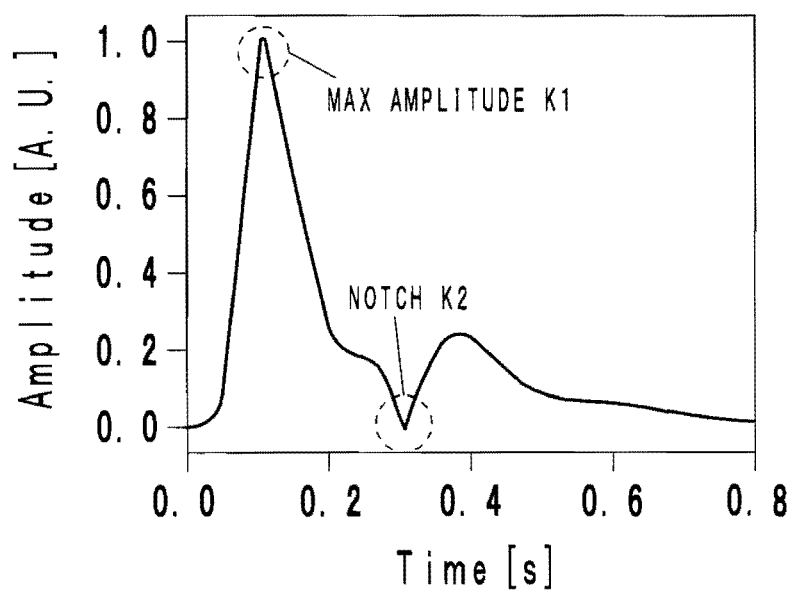

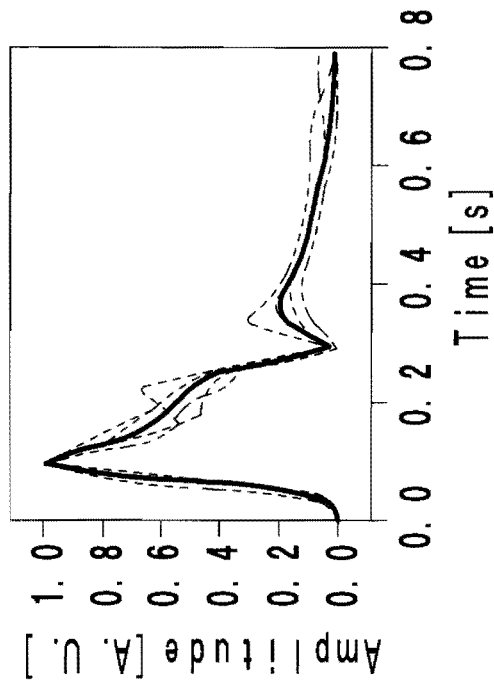
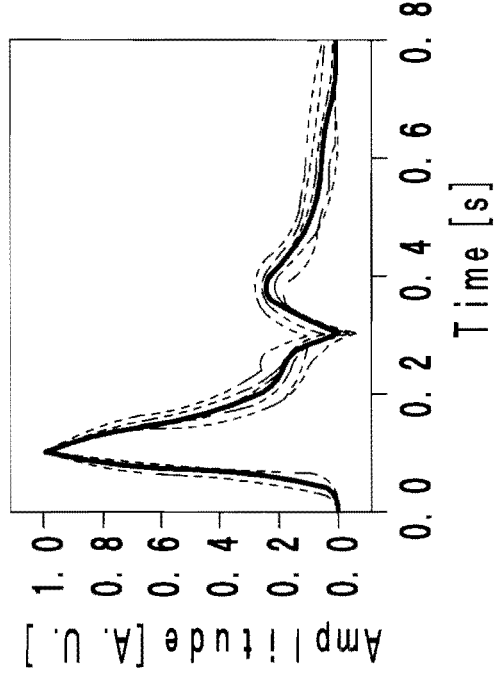
FIG. 10(a) SUBJECTS IN THEIR 20S
FIG. 10(b) SUBJECTS IN THEIR 60S
BLOOD FLOW VELOCITY WAVEFORMS OF INDIVIDUAL SUBJECTS (DOTTED LINES) & AVERAGE BLOOD FLOW VELOCITY WAVEFORM (SOLID LINE)

RESULT OF BREAKDOWN OF PULSE WAVE OF SUBJECT IN HIS/HER 20S

RESULT OF BREAKDOWN OF PULSE WAVE OF SUBJECT IN HIS/HER 60S

ARTERIOSCLEROSIS EVALUATING APPARATUS

CROSS REFERENCE TO RELATED APPLICATIONS

The present application claims priority to Japanese Patent Application No. 2008-223847 filed Sep. 1, 2008, and to International Application PCT/JP2009/065125 filed Aug. 29, 2009, the entire contents of these applications being incorporated herein by reference in their entirety.

FIELD OF THE DISCLOSURE

The present disclosure relates to an apparatus for evaluating vascular function, for example, the degree of arteriosclerosis.

BACKGROUND

In modern society, cardiovascular diseases originating from arteriosclerosis are increasing with changes in lifestyle and aging. However, medical care systems for early detection of these diseases are still undeveloped. Evaluation on the softness of blood vessel walls is very important for diagnosis of arteriosclerosis. At the present, image diagnostic methods by the use of MRI's and X-ray CT scans, and pulse wave velocity method are generally adopted for the diagnosis of arteriosclerosis. However, tests with MRIs and X-ray CT scans generally are costly, and these methods are not suitable for daily monitoring.

The pulse wave velocity method is based on the fact that the propagation velocity of the pulse wave changes according to the hardness/softness of blood vessel walls, and this pulse wave velocity method is generally used in medical practice, since a test using pulse wave velocity method is easy to conduct and also convenient. However, the relationship between age and pulse wave velocity is indistinct, and the accuracy of the diagnosis by this method is regarded as low, especially from the standpoint of prevention and in view of individual differences.

Japanese Patent Laid-Open Publication No. 2004-113593 proposes an apparatus including a pulse wave detection device to be attached to a specified site on a living body, and a compression device disposed downstream from the pulse wave detection device to suppress the blood flow by compressing another site on the living body. While the compression device is suppressing the blood flow, the pulse wave detection device detects the peak of a traveling wave component of the pulse wave and the peak of a reflected wave component of the pulse wave, and the apparatus evaluates the degree of arteriosclerosis based on the detection results. More specifically, a cuff incorporating a first compression bag and a second compression bag is attached to an upper arm, and, while the blood flow is stopped by the second compression bag, the upper arm pulse wave is detected by the first compression bag. This upper arm pulse wave is a synthetic wave of the traveling wave and the reflected wave that is generated at the site where the second compression bag is attached. The harder the artery is, the greater the reflected wave is, and the faster the speed of the reflected wave is. The time difference between the peak of the traveling wave component and the peak of the reflected wave component and the intensity ratio of these wave components to each other are calculated by use of an artery hardness calculation means. From the facts above, the calculated time difference and intensity ratio depend on the hardness of the artery, and it is considered that evaluation of the degree of arteriosclerosis is possible in this way.

Japanese Patent Laid-Open Publication No. 2006-158426 proposes another apparatus for evaluating the vascular function. For example, a first pulse wave detection device is attached to an upper arm, and a second pulse wave detection device is attached to a knee. Supposing that the time from a rise to a peak of the pulse wave of the elastic artery detected by the first pulse wave detection device is tp1 and that the time from a rise to a peak of the pulse wave of the elastic artery detected by the second pulse wave detection device is tp2, the time tp1 is almost equal to the time tp2 in normal cases. However, if the subject has arteriosclerosis, the peak of the pulse wave detected by the second pulse wave detection device comes earlier, and if the subject has arterial obstruction, the peak of the pulse wave detected by the second pulse wave detection device comes later. It is considered that evaluation of the vascular function is possible in this way.

SUMMARY

Embodiments described in the present disclosure provide an apparatus capable of easily separating pulse wave data detected at one measurement site into an incident wave and a reflected wave and capable of easily determining and evaluating the degree of arteriosclerosis.

According to an embodiment, an arteriosclerosis evaluating apparatus includes a pulse wave detection device adapted to detect a pulse wave transmitted through an artery at one point of a living body, a breakdown means or device adapted to perform fitting of the pulse wave detected by the pulse wave detection device with a fitting function so as to break down the pulse wave into a plurality of developed waves, and an evaluation device adapted to evaluate a degree of arteriosclerosis from amplitude intensities of the developed waves broken down from the pulse wave.

The pulse wave is a pressure wave transmitted through blood vessels that appears as a displacement on the body surface. The pulse wave includes an incident wave component that is a forward traveling wave generated by the blood ejection from the heart and a reflected wave component generated by arrival of the forward traveling wave at the periphery and reflection thereof from the periphery. Each of the wave components will be hereinafter referred to respectively as an incident wave and a reflected wave.

The reflected wave depends strongly on the viscoelasticity of the blood vessels and changes significantly according to the hardness of the blood vessel walls since the reflected wave reaches the periphery and reflects therefrom. Therefore, it is considered that evaluation of the hardness of blood vessels becomes possible by separating the pulse wave into an incident wave and a reflected wave and by examining the reflected wave.

According to an embodiment, first, the pulse wave transmitted through an artery can be detected at one point of a living body by the pulse wave detection device, for example, as a displacement signal. The pulse wave detection device may be a known pulse wave sensor that outputs a displacement signal or may be a sensor, such as a piezoelectric transducer.

When a piezoelectric transducer that outputs a velocity signal is used, a displacement signal can be obtained by performing time integration of the velocity signal. The piezoelectric transducer can be constructed to detect the pulse wave either as a velocity signal or as a displacement signal. The use of a piezoelectric transducer that detects the pulse wave as a velocity signal is preferred.

In order to measure a minute displacement of the skin surface such as the pulse wave, it is necessary to amplify the measured displacement. However, even if the subject is at rest during the measurement, it is likely that fine noise occurs due to breathing or movement of the body. The detection of the pulse wave as a velocity signal has a strong resistance to noise and permits elimination of DC fluctuation, thereby resulting in suppressing measurement errors. The pulse wave detected in this way is a synthetic wave including an incident wave and a reflected wave.

Next, the pulse wave (i.e., synthetic wave) including an incident wave and a reflected wave is fitted with a fitting function, and thereby the pulse wave can be broken down into a plurality of developed waveforms.

In breaking down the pulse wave, the fitting function can be used first so as to indentify the incident wave. The fitting function may be a nonlinear fitting function or may be a uniquely prepared model function. The nonlinear fitting function may be selected according to the pulse waveform, for example, from exponential Gaussian functions, Gauss function, Voigt functions, log-normal functions, Lorentz functions, etc.

The model function may be prepared, for example, in the following ways: incident wave data of a plurality of people in various age groups from young to old are collected by use of medical equipments, and typical model functions for the respective age groups are calculated from these data.

In evaluating the degree of arteriosclerosis of a person, one of the prepared model functions can be selected according to the age of the tested person, and the selected model function can be used for the fitting of the detected pulse wave. Further, the model functions may be adapted for various measurement sites. It is considered that the first rise of the pulse wave corresponds to an incident wave, and therefore, it is possible to identify the incident wave by fitting the first rise with a fitting function. Thereafter, the incident wave can be subtracted from the pulse wave, so that the reflected wave can be calculated.

An incident wave estimated from a blood flow velocity waveform may be used as the model function. For example, blood flow velocity waveforms of a plurality of subjects in each age group can be obtained by actual measurements, and the blood flow velocity waveforms can be normalized to calculate an average blood flow velocity waveform for the age group. Then, the incident wave can be estimated from the average blood flow velocity waveform.

More specifically, first, the blood flow velocities of a plurality of subjects in each age group can measured by use of the Doppler function of an ultrasonic diagnosis device. The waveforms of the measured blood flow velocities can be normalized so as to equalize the time intervals between the respective maximum amplitudes and the respective notches of the blood flood velocity waveforms, and thereby, an average blood flow velocity waveform can be calculated.

A reason for using maximum amplitude values is that these values are the maximum peaks of the blood flow velocity waveforms and are noticeable. A reason notches are used is that the notches are of similar shapes regardless of the age groups of the subjects and are noticeable. The notch shows the regurgitation from the aorta to the left ventricle that occurs after completion of ejection of blood by closure of the aortic valve at the end of a systolic phase. The time for one cycle of the blood flow waveform depends on the heart rate. Therefore, by normalizing the blood flow velocity waveforms so as to equalize the time intervals between the maximum amplitudes and the notches, variations due to the heart rate can be eliminated.

The average blood flow velocity waveform obtained in the above-described manner can then be converted into an inner pressure waveform (i.e., time waveform of intravascular pressure). This conversion into the inner pressure waveform is possible, for example, by using a series of expressions of one-dimensional fluid model and an equation of motion.

Next, the inner pressure waveform can be converted into a displacement signal of the skin surface by use of a complex elastic modulus. As a model of the complex elastic modulus, for example, a generalized Voigt model, a Voigt model or the like can be used.

The displacement signal obtained by the conversion can be assumed to represent the incident wave generated by an ejection of the blood from the heart of the subject. The blood flows substantially in one direction from the heart to the periphery, and it can be considered that the displacement information obtained from the one-directional blood flow is closely related to the displacement information of the incident wave component of the pulse wave generated from the heart like the blood flow. The incident wave estimated in this way is fitted to the first wave of the pulse wave, and the incident wave is subtracted from the pulse wave, whereby the reflected wave can be calculated.

From the amplitude intensities (i.e., peak intensities) of the incident wave and the reflected wave obtained in this manner, the degree of arteriosclerosis can be evaluated. For example, the difference between the amplitude intensity of the reflected wave and that of the incident wave or the ratio of the amplitude intensity of the reflected wave to that of the incident wave is calculated, and the degree of arteriosclerosis is evaluated from the difference or the ratio.

As arteriosclerosis progresses, generally, the viscoelasticity of blood vessels is lowered, and accordingly, it is likely that the amplitude intensity of the reflected wave becomes higher. Therefore, it is possible to evaluate the degree of arteriosclerosis by comparing the incident wave and the reflected wave in amplitude intensity.

Further, by normalizing the amplitude of the incident wave in fitting the incident wave, after the fitting, the amplitude of the reflected wave and the incident wave can be obtained as a ratio thereof. Thus, the amplitude can be compared with a reference value, and in this manner, the degree of arteriosclerosis can be evaluated easily.

The breakdown device may be further adapted to break down the reflected wave into a plurality of reflected waves by use of a fitting function, and the evaluation device may determine and evaluate the degree of arteriosclerosis from the amplitude intensities of the incident wave and the first reflected wave of the plurality of reflected waves. It can be considered that the reflected wave is composed of a plurality of different waveforms, and the reflected wave can be broken down into a plurality of developed waves by fitting with a fitting function. In this case, the wave that reaches the measurement site first is considered to be the most affected by the hardness of the artery, and by comparing the amplitude intensities of the incident wave and the first reflected wave, more detailed information on the degree of arteriosclerosis can be obtained.

Devices that can detect the pulse wave may be used as the pulse wave detection device. For example, when a piezoelectric transducer, which is small and inexpensive compared with a pulse wave sensor for medical use, is used, it is possible to detect the pulse wave only by bringing the piezoelectric transducer in contact with the skin surface of a human body, and the subject under testing feels no pain and suffers no injury. Also, the piezoelectric transducer does not detect the pulse pressure but detects the pulse vibration (i.e., displacement information) directly. Thus, the use of a piezoelectric transducer permits easier and more accurate detection of the pulse wave.

As described above, the pulse wave on a body surface can be detected with a single pulse wave detector, and the waveform of the detected pulse wave can be fitted and broken into a plurality of developed waveforms. Then, from the amplitude intensities of the developed waveforms, the degree of arteriosclerosis can be evaluated. Thus, an easy-to-use and inexpensive arteriosclerosis evaluating apparatus can be realized.

With the arteriosclerosis evaluating apparatus, the pulse wave is detected at only one point of a body, and measurement errors due to variations in the distance between two or more measurement points do not occur. Further, since a compression device for stopping the pulsation is not required, measurement errors due to variations in the compression force do not occur. Also, it is possible to take pulse wave data from subjects without causing the subjects pain or injury and accordingly without causing anxiousness. Therefore, the arteriosclerosis evaluating apparatus can be used as a home checkup device for evaluating the vascular function daily.

BRIEF DESCRIPTION OF THE DRAWINGS

FIG. 1 is a system diagram of an arteriosclerosis evaluating apparatus according to a first exemplary embodiment.

FIG. 2 is a schematic view of an exemplary piezoelectric transducer.

FIG. 3 is an internal circuit diagram of the evaluating apparatus according to the first exemplary embodiment.

FIG. 6(a) is a graph showing prepared incident wave model functions for young people according to a second exemplary embodiment.

FIG. 6(b) is a graph showing prepared incident wave model functions for old people according to the second exemplary embodiment.

FIG. 9 is a graph showing the blood flow velocity with the maximum amplitude and the notch marked.

FIG. 10(a) is a graph showing the measurement results of the blood flow velocities of 15 subjects in their twenties at the carotid arteries and the average blood flow velocity.

FIG. 10(b) is a graph showing the measurement results of the blood flow velocities of five subjects in their sixties at the carotid arteries and the average blood flow velocity.

DETAILED DESCRIPTION

Figure 4C:
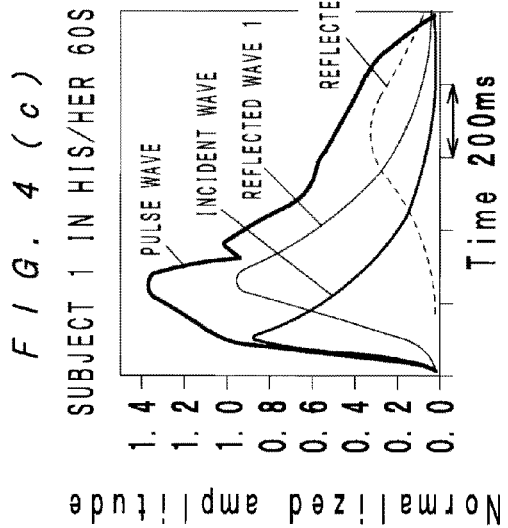
FIG. 4(c) is a graph showing the carotid pulse waves of subject 1 in his/her sixties, and waves are broken down from the pulse waves.

Many aspects of the invention are described in terms of sequences of actions to be performed by elements of a computer system or other hardware capable of executing programmed instructions. It will be recognized that in each of the embodiments, the various actions could be performed by specialized circuits (e.g., discrete logic gates interconnected to perform a specialized function), by program instructions, such as program modules, being executed by one or more processors, or by a combination of both. However, it is to be appreciated that the terms device and module used herein for elements in order to facilitate the disclosure only. Therefore, significant meanings or roles are not given to these terms themselves, and they each can be used to represent one or more circuit elements, one or more data processors, program instructions that can be executed by a data processing unit, or combinations thereof. Moreover, the invention can additionally be considered to be embodied within any form of computer readable carrier, such as solid-state memory, magnetic disk, and optical disk containing an appropriate set of computer instructions, such as program modules, and data structures that would cause a processor to carry out the techniques described herein. A computer-readable medium would include the following: an electrical connection having one or more wires, magnetic disk storage, magnetic cassettes, magnetic tape or other magnetic storage devices, a portable computer diskette, a random access memory (RAM), a read-only memory (ROM), an erasable programmable read-only memory (EPROM or Flash memory), or any other medium capable of storing information. Thus, the various aspects of the invention may be embodied in many different forms, and all such forms are contemplated to be within the scope of the invention.

Applicant has recognized that improvements and modifications to conventional apparatuses are desirable. For example, according to the disclosure of the Japanese Patent Laid-Open Publication No. 2004-113593, in order to separate the traveling wave and the reflected wave from the pulse wave, while the blood flow in the artery is stopped by the second compression bag, the pulse wave is detected. In such a method, two kinds of devices, that is, the first compression bag with a measuring device and the second compression bag as a blood flow stopping device are necessary. Since the traveling wave and the reflected wave are separated from each other based on the time difference of the pulse wave transmitted through a propagation path between these two devices, the detection result is influenced by the distance between these two devices.

Further, the influence of the use of the second compression bag on the pulsation is not considered, and more specifically, the amplitude intensity of the reflected wave component differs with differences in the suppressing force of the second compression bag. Still further, since subcutaneous fat differs among individuals, the control of the compression force is difficult. Thus, this is inadequate as a method for identifying individual differences.

According to the disclosure of the Japanese Patent Laid-Open Publication No. 2006-158426, it is necessary to detect the pulse wave of a living body at an upper limb and at a lower limb. In the apparatus of the Japanese Patent Laid-Open Publication No. 2006-158426, the length of the pulsation path from the heart to the upper limb and the length of the pulsation path from the heart to the lower limb are supposed to be equal to each other, and the vascular function is evaluated by comparing the time difference between the peaks at the upper limb and at the lower limb. However, the length of the pulsation path from the heart to the upper limb and the length of the pulsation path from the heart to the lower limb differ among individuals, and therefore, the measurement accuracy is poor. Further, it is necessary to detect the pulse at two sites, and the measurement is not easy.

FIG. 1 shows an arteriosclerosis evaluating apparatus according to a first exemplary embodiment. The first exemplary embodiment is related to a method comprising obtaining a pulse waveform (i.e., synthetic wave) with a piezoelectric transducer 1 and separating the pulse waveform into an incident wave and a reflected wave. In this embodiment, the carotid pulse wave is detected by use of one piezoelectric transducer 1. The piezoelectric transducer 1 is a kind of acoustic sensor for converting the pulse wave transmitted through an artery into a velocity signal. The piezoelectric transducer 1 is connected to the arteriosclerosis evaluating apparatus body 5 through a wiring.

On the arteriosclerosis evaluating apparatus body 5, a display unit 5a for displaying evaluation results is provided. The display unit 5a displays the degree of arteriosclerosis of a subject as a numerical value, a symbol, a graph, etc. The measurement site is not limited to the cervical region, and may be any site such as a wrist, an ankle or a femoral region, as long as it is a region where the pulse wave can be detected.

An output signal of an electrocardiographic monitor, which is to obtain an electrical waveform of the heartbeat, may be connected to the arteriosclerosis evaluating apparatus 5 to check the synchronization of the pulse wave with the heartbeat.

FIG. 2 shows an example of the structure of the piezoelectric transducer 1. The piezoelectric transducer 1 is of a piezoelectric unimorph structure. The piezoelectric transducer 1 has a bottomed tubular case 10, and the bottom 11 is configured to serve as a vibration surface. A piezoelectric ceramic element 12 is fixed to the inner surface of the bottom 11, and the outer surface of the bottom 11 is brought into contact with the skin of a subject H. The opening of the case 10 is closed with a sealing material 13, and lead wires 14 are pulled out through the sealing material 13. It is to be noted that the piezoelectric transducer 1 is an example and not necessarily of the structure shown by FIG. 2.

FIG. 3 shows the internal circuit of the arteriosclerosis evaluating apparatus 5. The pulse wave (i.e., velocity signal) detected by the piezoelectric transducer 1 is amplified by an amplifier 50 disposed in the arteriosclerosis evaluating apparatus 5, and thereafter is inputted into a block 51. It is noted that the terminologies block and module can be used interchangeably herein.

In the block 51, the velocity signal is subjected to time integration and is converted into a displacement signal. This displacement signal is a synthetic wave including an incident wave and a reflected wave existing in the pulse wave. A pulse wave sensor that outputs a displacement signal may be used in place of the piezoelectric transducer 1.

The displacement signal (i.e., pulse wave) obtained in the block 51 is sent to a block 52, where the displacement signal is broken down into a plurality of developed waveforms (i.e., incident wave and reflected wave). For the breakdown, a multi-peak fitting method is adopted. The multi-peak fitting method is a method of breaking down a synthetic waveform into developed waveforms by using a fitting function. In this embodiment, the multi-peak fitting method is used to break down the pulse wave into an incident wave and a reflected wave.

As the fitting function, an exponential Gaussian function, which is regarded to be the closest to the incident wave, is used, and the incident wave is first approximated by using the exponential Gaussian function. Next, the reflected wave is obtained by subtracting the incident wave from the pulse wave, and the obtained reflected wave is broken down into a plurality of developed waveforms by use of an exponential Gaussian function. The fitting function can be selected from various types of non-linear fitting functions such as a Gauss function, a Voigt function, a log-normal function, a Lorentz function, etc. as well as the exponential Gaussian function, according to the waveform of the pulse wave.

By the multi-peak fitting method, the displacement signal obtained in the block 51 can be broken down into an incident wave and a reflected wave, and thus, the pulse wave can be regarded as a synthetic wave of the incident wave and the reflected wave.

As mentioned, in the block 52, it is possible that the reflected wave separated from the pulse wave is further broken down into a plurality of developed waveforms.

In a block 53, the incident wave and the reflected wave obtained in the block 52 are compared with each other in amplitude intensity (i.e., the peak value), and the comparison result is sent to a block 54, where the degree of arteriosclerosis is evaluated.

Figure 4D:
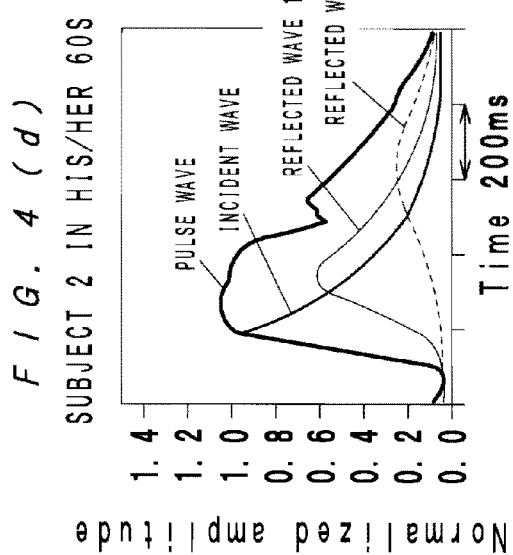
FIG. 4(d) is a graph showing the carotid pulse waves of subject 2 in his/her sixties, and waves are broken down from the pulse waves.
Figure 4A:
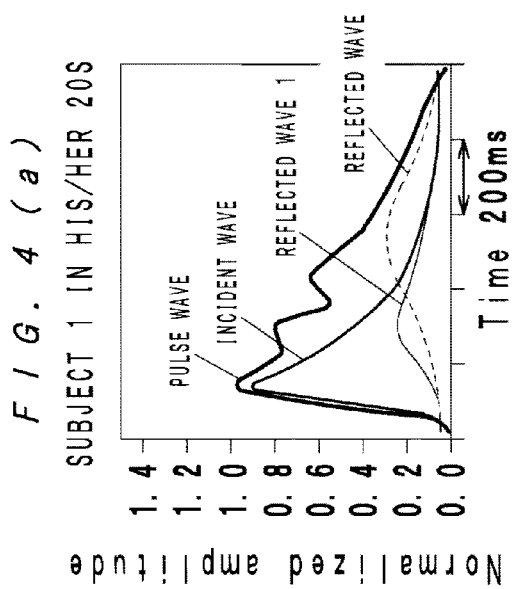
FIG. 4(a) is a graph showing the carotid pulse waves of subject 1 in his/her twenties, and waves are broken down from the pulse waves.
Figure 4B:
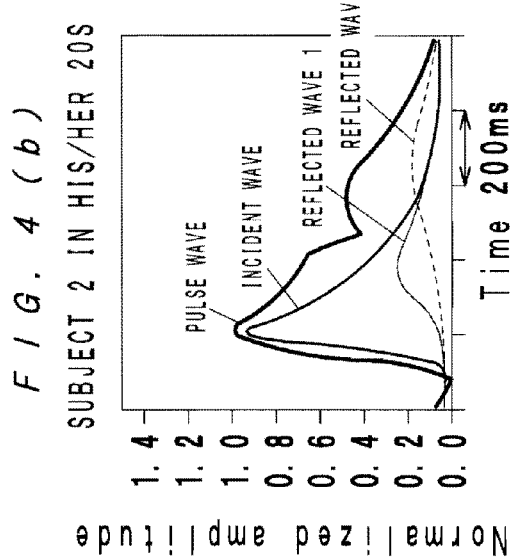
FIG. 4(b) is a graph showing the carotid pulse waves of subject 2 in his/her twenties, and waves are broken down from the pulse waves.
Figure 5:
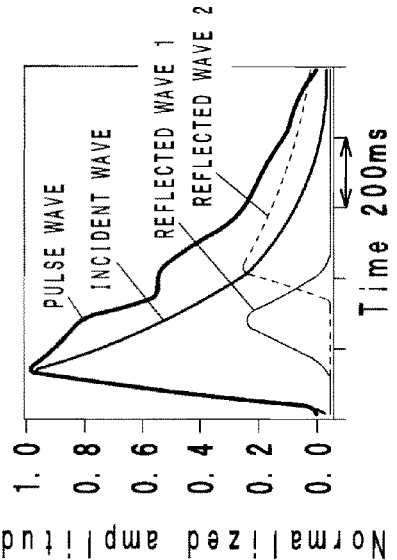
FIG. 5(a) is a graph showing the wrist pulse waves of subject 1 in her/her twenties, and waves are broken down from the pulse waves.
FIG. 5(b) is a graph showing the wrist pulse waves of subject 2 in her/her twenties, and waves are broken down from the pulse waves.
FIG. 5(c) is a graph showing the wrist pulse waves of subject 1 in her/her sixties, and waves are broken down from the pulse waves.
FIG. 5(d) is a graph showing the wrist pulse waves of subject 2 in her/her sixties, and waves are broken down from the pulse waves.
Figure 5:
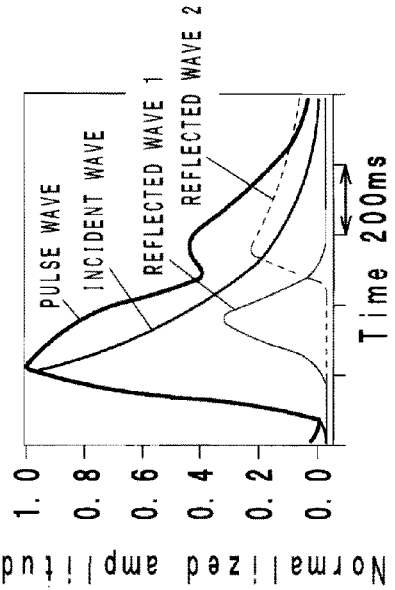
Figure 5:
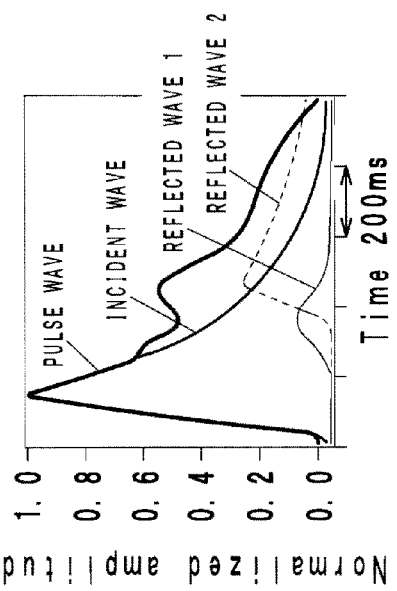
Figure 5:
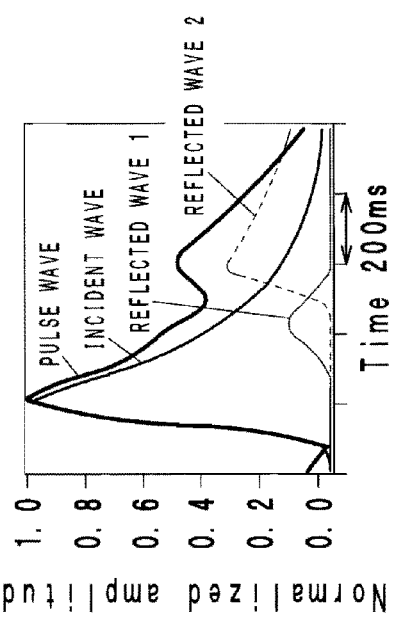

FIGS. 4(a) to 4(d) show the results of experiments that were carried out to detect the carotid pulse waves of two subjects in their twenties and two subjects in their sixties. FIG. 4(a) shows the result of the experiment carried out toward the subject 1 in his/her twenties, and FIG. 4(b) shows the result of the experiment carried out toward the subject 2 in his/her twenties. FIG. 4(c) shows the result of the experiment carried out toward the subject 1 in his/her sixties, and FIG. 4(d) shows the result of the experiment carried out toward the subject 2 in his/her sixties.

In each graph of FIGS. 4(a) to 4(d), the heavy line shows the detected pulse wave, and the thin line shows waves broken down from the pulse wave. In the cases of the subjects in their sixties, the maximum peak of the carotid pulse wave is not identical with the peak of the incident wave, and therefore, fitting of the incident wave was carried out at the first inflection point from the rise of the wave. In the experiments, each of the reflected waves was further broken down into two waves. However, further breakdowns of the reflected waves may not be carried out, or each of the reflected waves may be broken down into three or more waves.

In each of the graphs, the obtained waves were normalized with the maximum amplitude of the incident wave set to 1. In the cases of the subjects in their twenties, when the amplitude intensity of the incident wave is set to 1, the amplitude intensity of the first reflected wave 1 was about 0.2 to 0.3. In the cases of the subjects in their sixties, however, when the amplitude intensity of the incident wave is set to 1, the amplitude intensity of the first reflected wave 1 was about 0.6 to 1.0.

Between the cases of the subjects in their twenties and the cases of the subjects in their sixties, a significant difference was found in the amplitude intensity of the first reflected wave 1, and no significant difference was found in the amplitude intensity of the second reflected wave 2.

As arteriosclerosis progresses, generally, blood vessel walls become harder, and attenuation of the reflected wave becomes smaller. Thus, it is considered that the blood vessel walls of the subjects in their sixties are hard compared with the subjects in their twenties, thereby resulting in a small attenuation of the reflected wave during propagation and an increase in the amplitude intensity of the first reflected wave 1. By such a method, the hardness/softness of blood vessel walls can be evaluated.

FIGS. 5(a) to 5(d) show the results of experiments that were carried out to detect the wrist pulse waves of the two subjects in their twenties and the two subjects in their sixties who were the same persons subjected to the experiments shown by FIGS. 4(a) to 4(d). Both in the cases of the subjects in their twenties and in the cases of the subjects in their sixties, the maximum peak of the wrist pulse wave is identical with the peak of the incident wave, and fitting of the incident wave was carried out at the peak. In the cases of the wrist pulse wave, the amplitude of the first reflected wave 1 is relatively small compared with the cases of the carotid pulse wave. However, it is clearly seen that the amplitude intensity of the first reflected wave 1 in the cases of the subjects in their sixties is larger than that in the cases of the subjects in their twenties. Specifically, the amplitude intensity (ratio) of the reflected wave 1 in the cases of the subjects in their twenties is about 0.1, while that in the cases of the subjects in their sixties is about 0.2 to 0.3. Thus, from the amplitude intensity of the reflected wave 1, the degree of arteriosclerosis can be evaluated.

In the second reflected wave 2 of the wrist pulse wave, there is no significant difference between the subjects in their twenties and the subjects in their sixties. Thus, only with the wrist pulse wave, the degree of arteriosclerosis can be evaluated from the amplitude intensity of the first reflected wave 1.

In a second exemplary embodiment, a uniquely prepared model function is used as the fitting function. As is apparent from FIGS. 4(a)-4(d) and 5(a)-5(d), the pulse waveform varies according to the age group (or the degree of arteriosclerosis), and it is considered that the waveform of the incident wave also varies according to the age group.

In the first exemplary embodiment, the same fitting function, for example, an exponential Gaussian function is used for all age groups. In the second exemplary embodiment, however, different fitting functions (i.e., model functions) are used for different age groups.

The model functions may be prepared by using medical data within the public domain. Alternatively, incident wave data of a plurality of people from young to old may be collected by use of an ultrasonic diagnosis apparatus so that statistical incident wave data can be obtained, and the model functions for different age groups may be prepared based on the statistical data.

In addition to the age group, the model function used may be varied according to the sex. Furthermore, even with the same person, the carotid pulse wave and the wrist pulse wave have different waveforms, and therefore, different model functions may be used for different measurement sites.

FIGS. 6(a) and 6(b) show examples of incident wave model functions prepared in such a way. FIG. 6(a) shows an incident wave model function for young people, and FIG. 6(b) shows an incident wave model function for old people. Such model functions are prepared for various age groups. One is selected from these model functions according to the age group of the person to be subjected to the evaluation of the degree of arteriosclerosis by use of this evaluation apparatus. Then, by fitting the pulse wave of the person with the selected model function, the incident wave is separated from the pulse wave. Thus, in this method, because the age of the examined person is taken into consideration, the incident wave can be identified accurately, and the reflected wave can be separated accurately, compared with the case of using a fitting function for general use, such as an exponential Gaussian function.

Figure 7A:
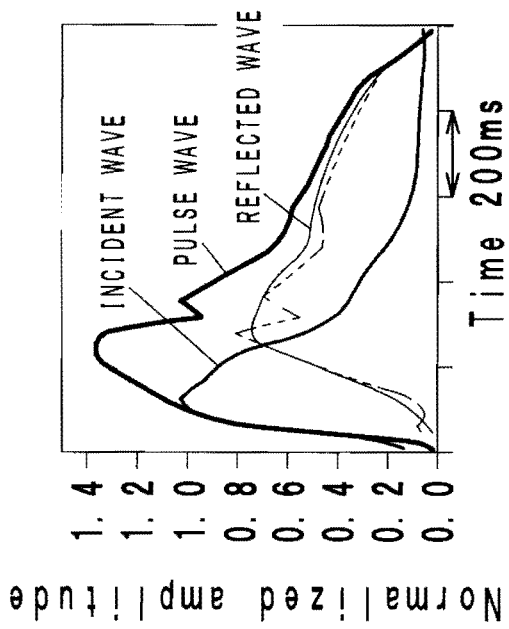
FIG. 7(a) is a graph showing the results of breakdowns of the carotid pulse waves of the subject 1 in his/her twenties shown in FIG. 4(a) into incident waves and reflected waves by using the model functions shown in FIG. 6(a).
Figure 7B:
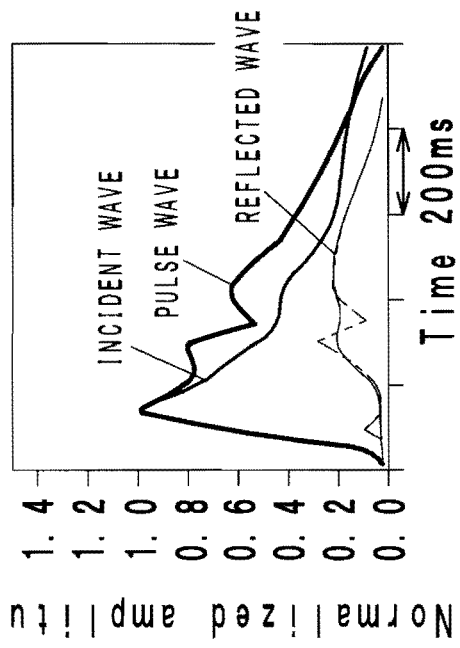
FIG. 7(b) is a graph showing the results of breakdowns of the carotid pulse waves of the subject 1 in his/her sixties shown in FIG. 4(c) into incident waves and reflected waves by using the model functions shown in FIG. 6(b).

FIGS. 7(a) and 7(b) show the results of fittings of the carotid pulse waves of the subject 1 in his/her twenties and the subject 1 in his/her sixties with the model functions shown by FIGS. 6(a) and 6(b). That is, the incident waves and the reflected waves broken down from their pulse waves as the results of the fittings by use of the model functions shown by FIGS. 6(a) and 6(b). Further, the reflected waves are smoothed so that the peaks can be identified easily.

In FIGS. 7(a) and 7(b)FIG., the reflected waves before the smoothing are indicated by dots, and the reflected waves after the smoothing are indicated by solid lines. As is apparent from FIGS. 7(a) and 7(b)FIG., when the amplitude intensity of each of the incident waves is assumed as 1, the amplitude intensity (i.e., ratio) of the reflected wave of the subject in his/her twenties is about 0.2, and that of the subject in his/her sixties is about 0.8. Thus, it is clear that there is a significant difference between these subjects in the amplitude intensity of the reflected wave. In the case of FIGS. 7(a) and 7(b)FIG., the degree of arteriosclerosis is evaluated from one reflected wave. However, the reflected wave may be further broken down into a plurality of waves by using a known fitting function, and the degree of arteriosclerosis may be evaluated from one of the broken-down waves.

Figure 8:
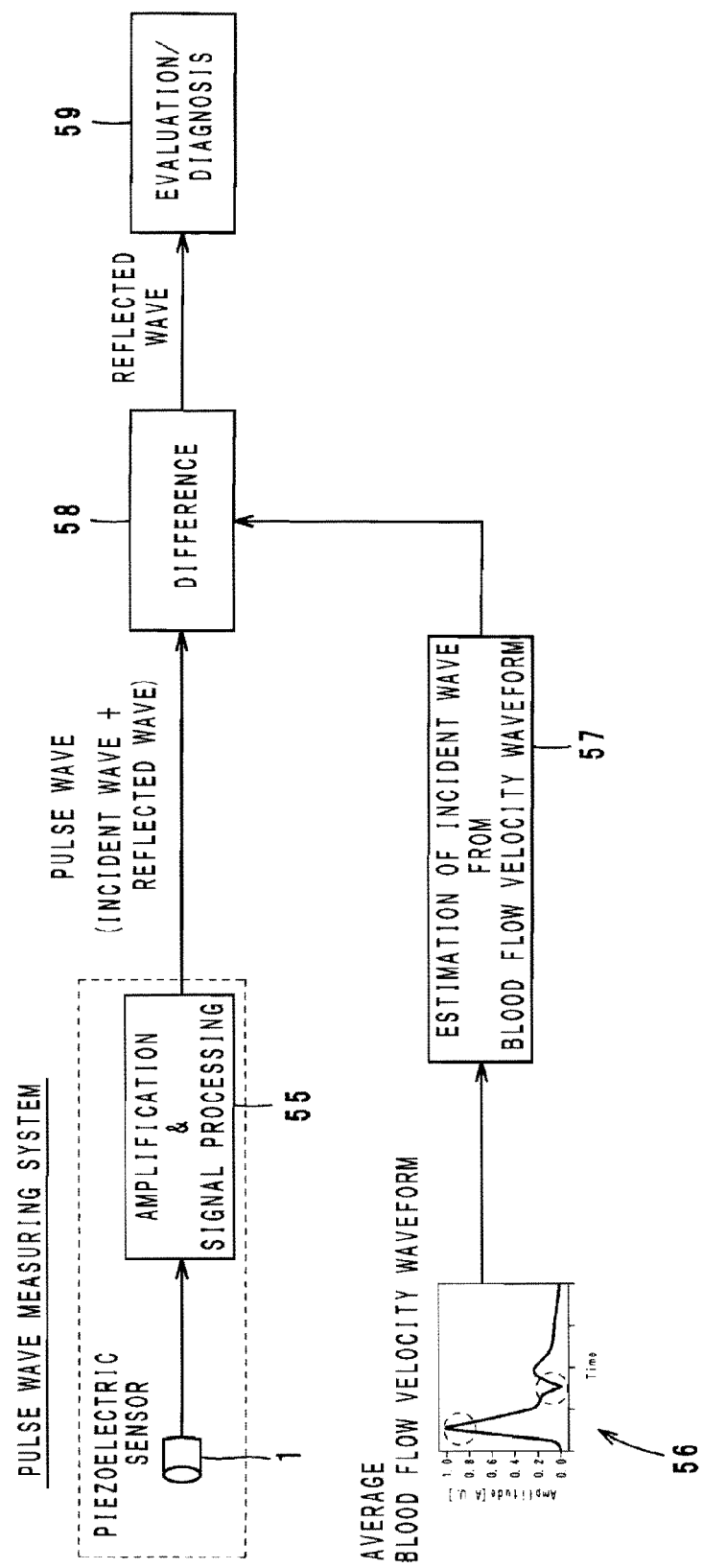
FIG. 8 is an internal circuit diagram of an arteriosclerosis evaluating apparatus according to a third exemplary embodiment.

FIG. 8 shows the structure of an arteriosclerosis evaluating apparatus according to a third exemplary embodiment. The third exemplary embodiment is an application of the second exemplary embodiment, and an incident wave calculated statistically from blood flow velocity data collected by use of an ultrasonic diagnosis apparatus. The pulse wave (i.e., velocity signal) detected by the piezoelectric sensor 1 is subjected to processes such as amplification and time integration in an amplification/signal processing block 55, so that the pulse wave is converted into a displacement signal. The pulse wave is a synthetic wave including an incident wave and a reflected wave.

Average blood flow velocity waveforms for various age groups were calculated statistically, and these waveforms are stored in a database 56. The average blood flow velocity waveform for each age group can be obtained, for example, by measuring the blood flow velocities of subjects in each age group by use of the Doppler function of an ultrasonic diagnosis device, and by normalizing the blood flow velocity waveforms obtained as the results of the measurements so that the time intervals between the respective maximum amplitude values and the respective notches of the waveforms will be equal to one another.

In a block 57, the incident wave is estimated based on the average blood flow waveform stored in the database 56. Specifically, first, the average blood flow waveform is converted into an inner pressure waveform (e.g., time waveform of the intravascular pressure). This conversion into the inner pressure waveform is possible by a known method using a series of expressions of one-dimensional fluid model and an equation of motion. In other words, alteration of the cross-sectional area of the blood vessel from moment to moment is estimated from the blood flow velocity, and the time waveform of the intravascular pressure is deduced from the relationship between the alteration of the cross-sectional area of the blood vessel from moment to moment and the intravascular pressure. Next, the time waveform of the intravascular pressure p is converted into a displacement signal ε of the skin surface by use of a generalized Voigt model shown below by expressions (1) and (2). The displacement signal ε obtained by the conversion indicates a displacement of the skin surface estimated from the blood flow velocity waveform and is assumed to represent the incident wave of the pulse wave generated by an ejection of the blood from the heart of the subject H.

$$p = \gamma_i \varepsilon_i + \eta_i \frac{d\varepsilon_i}{dt} \quad (1)$$

$$\varepsilon(t) = \sum_{i=1}^{n} e^{-\frac{\gamma_i}{\eta_i} t} \cdot \frac{1}{\eta_i} \int_0^t p e^{\frac{\gamma_i}{\eta_i} t} dt \quad (2)$$

However, the shift elasticity constant γ and the shift viscosity coefficient η depend on the age of the subject. For example, the shift elasticity constant γ for young people may be 5.6 kPA to 16.0 kPa, while that for old people may be 14.0 kPa to 40.0 kPa. The shift viscosity coefficient η both for young people and for old people may be 230,000 Pa·s to 1,100 Pa·s.

In this embodiment, the generalized Voigt model is used as the model of the complex elastic modulus for converting the intravascular pressure into a displacement signal of the skin surface, but it is to be noted that other models as well as the Voigt model may be used.

The pulse wave obtained in the block 55 and the incident wave obtained in the block 57 are sent to a block 58, where the incident wave is fitted to the pulse wave by the multi-peak fitting method, so that a difference is calculated. Specifically, the incident wave deduced in the block 57 is subtracted from the pulse wave (i.e., synthetic wave) obtained in the block 55, and thereby, the reflected wave is calculated. Then, the data of the reflected wave are sent to an evaluation/diagnosis block 59.

In the block 59, evaluation of the degree of arteriosclerosis or diagnosis of arteriosclerosis is made by comparing the incident wave with the reflected wave in amplitude intensity in the same way as described above in connection with FIG. 3, or by comparing the reflected wave with a reference value.

FIG. 9 is an example of the blood flow velocity waveform obtained as the result of a measurement. In this waveform, the first amplitude peak is the maximum amplitude peak K1, and the point where the amplitude is almost 0 is the notch K2. The maximum amplitude peak K1 and the notch K2 show the start and the end of a systole, respectively, in a cardiac cycle (e.g., a cycle of systole and diastole of the heart).

FIGS. 10(a) and 10(b) show the results of blood flow velocity measurements. The waveforms in FIG. 10(a) show the blood flow velocities at the carotid arteries of 15 subjects in their twenties, and the waveforms in FIG. 10(b) show the blood flow velocities at the carotid arteries of 6 subjects in their sixties.

In each of the graphs of FIGS. 10(a) and 10(b), the broken lines show waveforms of the measured blood flow velocities of the respective subjects, and the solid line shows a waveform of average blood flow velocity. The blood flow velocity waveforms of the respective subjects are different in time for one cycle since the heart rates of the subjects are different. Therefore, normalization is carried out to equalize the time intervals between the respective maximum amplitude peaks K1 and the respective notches of the blood flow velocity waveforms of the subjects, and then, averaging is carried out to obtain the average blood flow velocity waveform.

Figure 11:
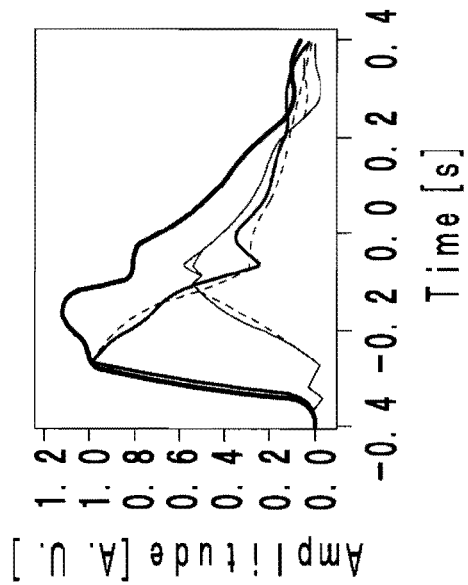
FIG. 11(a) is a graph showing the carotid pulse wave, the incident wave and the reflected wave of a subject in his/her twenties.
FIG. 11(b) is a graph showing the carotid pulse wave, the incident wave and the reflected wave of a subject in his/her sixties.
Figure 11:
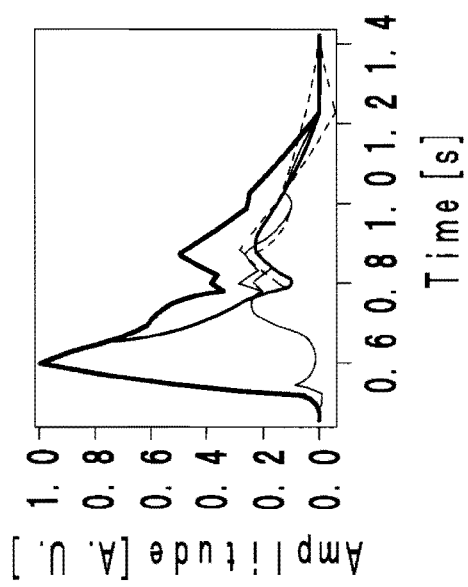

FIG. 11(a) shows waveforms of the carotid pulse wave, the incident wave and the reflected wave of another subject in his/her twenties, and FIG. 11(b) shows waveforms of the carotid pulse wave, the incident wave and the reflected wave of another subject in his/her sixties.

In each graph of FIGS. 11(a) and 11(b), the incident wave and the reflected wave shown by solid lines were obtained in the following way: the blood flow velocity was actually measured by use of an ultrasonic diagnosis device; the incident wave was estimated from the blood flow velocity waveform obtained as the result of the measurement; and the reflected wave was calculated by subtracting the incident wave from the pulse wave. The incident wave and the reflected wave shown by broken lines were obtained without performing measurements by use of an ultrasonic diagnosis device. Specifically, the incident wave shown by the broken line was estimated from the average blood flow velocity waveform shown by FIGS. 10(a) and 10(b), and the reflected wave shown by the broken line was calculated by subtracting the incident wave from the pulse wave.

In the cases of young people, the difference between the result of the calculation based on the actual measurement of the blood flow velocity and the result of the calculation by using the average blood flow velocity waveform was about ±0.04 in the amplitude of the reflected wave, which verified that the estimation of the incident wave from the average blood flow velocity waveform is highly accurate.

In the cases of old people, the difference between the result of the calculation based on the actual measurement of the blood flow velocity and the result of the calculation by using the average blood flow velocity waveform was about ±0.07 in the amplitude of the reflected wave, which is larger than that in the cases of young people. However, it is considered that this larger difference is due to a smaller number of subjects for calculating the average blood flow velocity waveform, and it was still found that the estimation of the incident wave by use of the average blood flow velocity waveform is effective.

According to the embodiments, the pulse wave is detected on the skin surface with a single pulse wave detector, and the detected pulse wave is broken down into an incident wave and a reflected wave. This method does not require specialized technical knowledge, and an easy-to-use and inexpensive arteriosclerosis evaluating apparatus can be realized.

Further, use of a piezoelectric transducer as the pulse wave detector can reduce cost significantly compared with the case of using a known medical amorphous pulse wave sensor. Also, since the piezoelectric transducer does not detect the pressure of the pulse but detects the vibration (displacement information) of the pulse, the detection results are hardly affected by the skin at the measurement site, and stable measurement results can be obtained. Additionally, a compression device for stopping the pulsation is not required, and subjects of the measurements according to embodiments have no pain and no injury. Accordingly, with the apparatus according to an embodiment consistent with this disclosure, people can take data without regard to the measurement, and the apparatus can be used daily as a home checkup device for evaluating the vascular function.

According to embodiments consistent with this disclosure, a pulse wave detecting device is not limited to a combination of a piezoelectric transducer and an integrator, and any sensor, such as a known pulse wave sensor, can be used as long as it can detect the pulse wave transmitted through the artery. When the pulse wave is detected as a velocity signal as in the case of using a piezoelectric transducer, the blood flow velocity waveform may be converted into a velocity signal of the skin surface, and then, the velocity signal may be assumed as the incident wave.

In the third exemplary embodiment, the blood flow velocity waveform is converted into an inner pressure waveform, and the inner pressure waveform is further converted into a displacement signal of the skin surface by use of a complex elastic modulus to estimate the incident wave. However, the following method may be adopted in place of the above-mentioned method: the pulse wave is detected as a velocity signal; a blood flow velocity waveform is converted into a velocity signal of the skin surface, and this velocity signal is estimated as the incident wave; fitting of the incident wave to the pulse wave is performed to separate the reflected wave.

In the exemplary embodiments described above, the degree of arteriosclerosis is evaluated based on the amplitude intensity of the reflected wave. However, the degree of arteriosclerosis may be evaluated based on waveform information about changes of the reflected wave, such as the time length (i.e., pulse width) of the reflected wave.

Further, in the embodiments above, the pulse wave is detected as a displacement signal, and the displacement signal is fitted with a fitting function so as to break down the signal waveform into a plurality of developed waveforms. However, the pulse wave may be detected as a velocity signal waveform, and the velocity signal waveform may be broken down into a plurality of developed waveforms, which will be factors of evaluation.

While preferred embodiments have been described above, it is to be understood that variations and modifications will be apparent to those skilled in the art without departing from the scope and spirit of the disclosure. The scope of the disclosure, therefore, is to be determined solely by the following claims and their equivalents.

What is claimed is:

1. An arteriosclerosis evaluating apparatus comprising:
a pulse wave detection device adapted to detect a pulse wave transmitted through an artery at one point of a living body;
a breakdown device adapted to perform fitting of the pulse wave detected by the pulse wave detection device with a fitting function to break down the pulse wave into a plurality of developed waves; and
an evaluation device adapted to evaluate a degree of arteriosclerosis from amplitude intensities of the developed waves broken down from the pulse wave,
wherein the breakdown device is further adapted to fit a first wave of the pulse wave with the fitting function to identify an incident wave, and to subtract the incident wave from the pulse wave to calculate a reflected wave.

2. The arteriosclerosis evaluating apparatus according to claim 1, wherein the pulse wave detection device detects the pulse wave as a displacement signal.

3. The arteriosclerosis evaluating apparatus according to claim 1, wherein the fitting function is an exponential Gaussian function.

4. The arteriosclerosis evaluating apparatus according to claim 1, wherein the fitting function is a prepared model function.

5. The arteriosclerosis evaluating apparatus according to claim 4, wherein the prepared model function is the incident wave prepared by measuring blood flow velocities of subjects in every age group, by calculating an average blood flow velocity waveform by performing normalization of waveforms of the measured blood flow velocities to equalize time intervals between respective maximum amplitude intensities and respective notches of the waveforms and by estimating the incident wave by use of the average blood flow velocity waveform.

6. The arteriosclerosis evaluating apparatus according to claim 5,
wherein the evaluation device evaluates the degree of arteriosclerosis from the amplitude intensity of the reflected wave or a comparison of the incident wave and the reflected wave in amplitude intensity.

7. The arteriosclerosis evaluating apparatus according to claim 1,
wherein the evaluation device evaluates the degree of arteriosclerosis from the amplitude intensities of the incident wave and the reflected wave.

8. The arteriosclerosis evaluating apparatus according to claim 7,
wherein the breakdown device is further adapted to break down the reflected wave into a plurality of reflected waves by use of the fitting function; and
wherein the evaluation device evaluates the degree of arteriosclerosis from the amplitude intensity of the incident wave and the amplitude intensity of the first reflected wave of the plurality of reflected waves.

9. The arteriosclerosis evaluating apparatus according to claim 1, wherein the pulse wave detection device includes a piezoelectric transducer adapted to detect the pulse wave as a velocity signal.

10. The arteriosclerosis evaluating apparatus according to claim 9, wherein the pulse wave detection device further includes an integrator adapted to perform time integration of outputs from the piezoelectric transducer.

11. The arteriosclerosis evaluating apparatus according to claim 2, wherein the fitting function is an exponential Gaussian function.

12. The arteriosclerosis evaluating apparatus according to claim 2, wherein the fitting function is a prepared model function.

13. The arteriosclerosis evaluating apparatus according to claim 12, wherein the prepared model function is an incident wave prepared by measuring blood flow velocities of subjects in every age group, by calculating an average blood flow velocity waveform by performing normalization of waveforms of the measured blood flow velocities to equalize time intervals between respective maximum amplitude intensities and respective notches of the waveforms and by estimating the incident wave by use of the average blood flow velocity waveform.

14. The arteriosclerosis evaluating apparatus according to claim 13,
wherein the evaluation device evaluates the degree of arteriosclerosis from the amplitude intensity of the reflected wave or a comparison of the incident wave and the reflected wave in amplitude intensity.

15. The arteriosclerosis evaluating apparatus according to claim 2, wherein the evaluation device evaluates the degree of arteriosclerosis from the amplitude intensities of the incident wave and the reflected wave.

16. The arteriosclerosis evaluating apparatus according to claim 3,
wherein the evaluation device evaluates the degree of arteriosclerosis from the amplitude intensities of the incident wave and the reflected wave.

17. The arteriosclerosis evaluating apparatus according to claim 4,
wherein the evaluation device evaluates the degree of arteriosclerosis from the amplitude intensities of the incident wave and the reflected wave.

18. The arteriosclerosis evaluating apparatus according to claim 15,
wherein the breakdown device is further adapted to break down the reflected wave into a plurality of reflected waves by use of the fitting function; and
wherein the evaluation device evaluates the degree of arteriosclerosis from the amplitude intensity of the incident wave and the amplitude intensity of the first reflected wave of the plurality of reflected waves.

19. The arteriosclerosis evaluating apparatus according to claim 16,
wherein the breakdown device is further adapted to break down the reflected wave into a plurality of reflected waves by use of the fitting function; and
wherein the evaluation device evaluates the degree of arteriosclerosis from the amplitude intensity of the incident wave and the amplitude intensity of the first reflected wave of the plurality of reflected waves.

20. The arteriosclerosis evaluating apparatus according to claim 17,
wherein the breakdown device is further adapted to break down the reflected wave into a plurality of reflected waves by use of the fitting function; and
wherein the evaluation device evaluates the degree of arteriosclerosis from the amplitude intensity of the incident wave and the amplitude intensity of the first reflected wave of the plurality of reflected waves.

* * * * *